United States Patent [19]

Weiner et al.

[11] 4,254,128
[45] Mar. 3, 1981

[54] 2-ADAMANTYL HYDRAZINES AND BIOCIDAL COMPOSITIONS THEREOF

[75] Inventors: Ben-Zion Weiner; Raul Suchi; Jeffrey Sterling, all of Jerusalem; Haim Yellin, Ramat Gan, all of Israel

[73] Assignee: Teva Pharmaceutical Industries Ltd., Jerusalem, Israel

[21] Appl. No.: 963,113

[22] Filed: Nov. 22, 1978

[30] Foreign Application Priority Data

Nov. 22, 1977 [IL] Israel ......................................... 53440

[51] Int. Cl.$^3$ ................... A61K 31/445; A61K 31/40; C07D 295/22

[52] U.S. Cl. ................................. 424/267; 260/239 B; 260/326.85; 424/244; 424/246; 424/248.4; 424/250; 424/258; 424/263; 424/273 R; 424/274; 424/312; 424/319; 424/327; 544/58.2; 544/59; 544/155; 544/380; 546/162; 546/203; 546/285; 560/117; 562/439; 562/499; 564/310; 564/459

[58] Field of Search ..................... 546/203; 260/326.85, 260/239 B, 239 AR; 424/244, 267, 274

[56] References Cited

U.S. PATENT DOCUMENTS

| | | | |
|---|---|---|---|
| 3,397,233 | 8/1968 | Cairns | 546/203 X |
| 3,703,537 | 11/1972 | Richter et al. | 546/203 X |
| 3,838,151 | 9/1974 | Grisar et al. | 260/326.85 X |
| 4,061,774 | 12/1977 | Chakrabarti et al. | 546/203 X |
| 4,100,170 | 7/1978 | Shetty | 424/330 X |

Primary Examiner—Henry R. Jiles
Assistant Examiner—Richard A. Schwartz
Attorney, Agent, or Firm—Browdy and Neimark

[57] ABSTRACT

The invention provides novel 2-adamantyl hydrazine derivatives of the general formula A

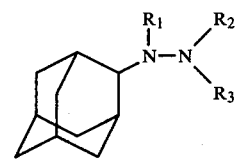

In this formula $R_1$ is hydrogen or a lower alkyl group of 1–4 carbon atoms; $R_2$ and $R_3$ are the same or different and are each hydrogen, an unsubstituted or substituted radical being a lower alkyl of 1–4 carbon atoms, a lower alkanoic acid radical of 2–4 carbon atoms or a lower alkyl ester thereof, adamantyl, aryl, aralkyl, in which the alkyl moiety has from 1–4 carbon atoms or an unsubstituted or substituted heterocyclic radical of aromatic character; or $R_2$ and $R_3$ together with the nitrogen atom to which they are attached form an unsubstituted or substituted non-aromatic cyclic radical.

The invention further provides pharmaceutically acceptable acid addition salts of the above compounds.

7 Claims, 2 Drawing Figures

Fig. 2

2-ADAMANTYL HYDRAZINES AND BIOCIDAL COMPOSITIONS THEREOF

The present invention relates to novel 2-adamantyl hydrazine derivatives, to pharmaceutically acceptable acid addition salts thereof and to methods of preparing the novel compounds and their salts.

Specifically the invention provides novel 2-adamantyl hydrazine derivatives of the general formula A in which $R_1$ is hydrogen or a lower alkyl group of 1–4 carbon atoms, $R_2$ and $R_3$ are the same or different and are each hydrogen, an unsubstituted or substituted radical being a lower alkyl of 1–4 carbon atoms, a lower alkanoic acid radical of 2–4 carbon atoms or a lower alkyl ester thereof, adamantyl, aryl, aralkyl in which the alkyl moiety has from 1–4 carbon atoms or an unsubstituted or substituted heterocyclic radical of aromatic character; or $R_2$ and $R_3$ together with the nitrogen atom to which they are attached from an unsubstituted or substituted non-aromatic cyclic radical; and pharmaceutically acceptable acid addition salts thereof.

The term "lower alkanoic acid radical" refers herein to a radical which is linked to the hydrazine nitrogen atom at one of its non-carboxylic carbon atoms, i.e. at a carbon atom forming part of the lower alkyl moiety of said radical.

When $R_2$ and/or $R_3$ is a lower alkyl ester of an alkanoic acid radical of 2–4 carbon atoms, the ester forming lower alkyl radical may, for example, be methyl, propyl, butyl.

Examples of heterocyclic radicals of aromatic character for which either of $R_2$ and $R_3$ may stand are pyridinyl, quinolinyl.

Examples of cyclic radicals formed by $R_2$, $R_3$ and the nitrogen atom to which they are attached are piperazino, piperidino, homopiperidino, pyrrolidino, morpholino, thiomorpholino, hydantoino, heptamethyleneimino radicals, all of which may be substituted.

Compounds of formula A in which $R_1$ is H can be prepared in accordance with the invention by reacting 2-adamantanone with a hydrazine compound in which one nitrogen is unsubstituted of the general formula B in which $R_2$ and $R_3$ have the same meanings as in the formula A, and reducing the resulting hydrazone. The reduction may be effected in any conventional way, e.g. with sodium cyanoborohydride, with lithium aluminum hydride or by catalytic hydrogenation, e.g. using any suitable conventional hydrogenation catalyst such as, for example, Adam's Catalyst.

This reaction is depicted in the following Reaction Scheme I in which $R_2$ and $R_3$ have the same meanings as in formula A:

Reaction Scheme I

This general method was applied in accordance with the present invention in the preparation of the following new 2-adamantyl hydrazine derivatives:

1-(2'-adamantyl)-2,2-dimethylhydrazine
1-(2'-adamantyl)-2-[1'-(2'-hydroxyethyl)]hydrazine
1-(2'-adamantyl)-2-butylhydrazine
1-(2'-adamantyl)-2-(adamant-1"-ylmethyl)hydrazine
1-(2'-adamantyl)-2-phenethylhydrazine
1-(2'-adamantyl)-2-phenylhydrazine
1-(2'-adamantyl)-2-(p-bromophenyl)hydrazine
2-(2'-adamantyl)-1-benzyl-1-phenylhydrazine
1-(2'-adamantyl)-2,2-diphenylhydrazine
1-(2'-adamantyl)-2-(m-trifluoromethylphenyl)hydrazine
1-(2'-adamantyl)-2-(o-carboxyphenyl)hydrazine
1-(2'-adamantyl)-2-(2"-pyridyl)hydrazine
1-(2'-adamantyl)-2-[4"-(7"-chloroquinolinyl)]hydrazine
1-(2'-adamantylamino)pyrrolidine
1-(2'-adamantylamino)piperidine
1-(2'-adamantylamino)homopiperidine
1-(2'-adamantylamino)heptamethyleneimine
4-(2'-adamantylamino)morpholine
4-(2'-adamantylamino)thiomorpholine
4-(2'-adamantylamino)thiomorpholine-1,1-dioxide
1-(2'-adamantylamino)piperazine
1-(2'-adamantylamino)-4-methylpiperazine
1-(2'-adamantylamino)-4-benzylpiperazine
1-(2'-adamantylamino)-4-(m-trifluoromethylphenyl)-piperazine
1-(2'-adamantylamino)hydantoin By another embodiment for the preparation of compounds of formula A in which $R_1$ is H, 2-adamantanone is condensed with a protected hydrazine compound in which one nitrogen is unsubstituted, the resulting protected hydrazone compound is reduced with an appropriate reducing agent, and the protecting group is split off. This embodiment will be referred to in the following as the "protected hydrazone embodiment". The protection may for example be by means of an acyl group such as, e.g. acetyl, benzoyl or t-butylcarbonyl. Where the protecting group is an acyl group it may be split off by means of acid hydrolysis, e.g. with hydrochloric acid or gaseous HCl in the presence of nitromethane. This embodiment of preparation of compounds according to the invention is depicted in part (a) of Reaction Scheme II below. In this reaction scheme the protecting group is assumed to be acetyl which is of course an example only. In this reaction scheme $R_2$ has the same meaning as in formula A:

Reaction Scheme II

By a modification of the protected hydrazone embodiment the protected hydrazone obtained as above is subjected to a substitution reaction by which the substituent $R_2$ is introduced which has the same meaning as in formula A, and the resulting substitution product is subjected to total reduction. For example, where $R_2$ is a lower alkyl the substitution reaction can be, e.g., effected by treatment with sodium hydride NaH followed by alkyl iodide $R_2I$. The total reduction in this embodiment can be effected with known strong reducing reagents such as for example lithium aluminum hydride. The foregoing modification of the protected hydrazone embodiment is depicted in part (b) of the above Reaction Scheme II.

Examples of compounds which were prepared in accordance with the foregoing modification are 1-(2'-adamantyl)-2,2'-dimethyl hydrazine, 1-(2'-adamantyl)-2-ethyl-2-methyl hydrazine and 1-(2'-adamantyl)-2,2-diethyl hydrazine.

By yet another modification of the protected hydrazone embodiment the protected and substituted hydrazone obtained as in the preceding modification is subjected to partial reduction, e.g. catalytic hydrogenation, and from the resulting product the protecting group is split off. Where the protecting group is an acyl it may be be split off by acidic hydrolysis, e.g. with aqueous hydrochloric acid. This modification of the protected hydrazone embodiment is depicted in part (c) of the above Reaction Scheme II.

By yet another modification of the protected hydrazone method serving for the preparation of novel compounds according to the invention in which $R_1$ is a lower alkyl radical (e.g. methyl), and $R_2$ is as in formula A, 2-adamantone is reacted with a protected hydrazine in which one nitrogen is unsubstituted to yield a corresponding protected hydrazone, the latter is partially reduced and the reduction product is subjected to a substitution reaction to introduce the radical $R_1$.

The reduction in this modification is again conventional, e.g. by sodium cyanoborohydride. Likewise, any suitable method for the introduction of an alkyl group $R_1$ into the $N_1$ position may be employed. By one particular method for the introduction of a methyl group the methylating agent is methyl fluorosulfonate in methyl acetate.

This modification is depicted in Reaction Scheme III in which the hydrazine bears a protecting group $R_4$, e.g. methyl or phenyl. From the resulting substitution product, the protecting group may be split off, e.g. with conc. hydrochloric acid as shown in part (a) of Reaction Scheme III. This procedure results in a 1-alkyl substituted 1-adamantylhydrazine.

Reaction Scheme IV

In this way there was synthesized, for example, 1-(2'-adamantyl)-1-methylhydrazine, the protecting group $R_4$ being, for example, phenyl.

By yet a further variation of this modification of the protected hydrazone embodiment the substituted protected adamantylhydrazine of the preceding modification is further substituted. For example where $R_2$ is a lower alkyl the substitution reaction can be effected by treatment with NaH followed by alkyl iodide, $R_2I$. From the resulting substitution product, the protecting group may be split off, e.g. with conc. HCl as shown in part (b) of Reaction Scheme III. This procedure results in a 1,2-disubstituted adamantylhydrazine. In this way there was synthesized, for example, 1,2-dimethyl-1-(2'-adamantyl)hydrazine, in which $R_1$ and $R_2$ are both methyl.

By yet a further variation of this modification of the protected hydrazone embodiment, the disubstituted protected adamantylhydrazine of the previous variation is subjected to reduction with a known strong reducing agent such as for example lithium aluminum hydride as in part (c) of Reaction Scheme III. In this way there was synthesized, for example, 1,2-dimethyl-2-ethyl-1-(2'-adamantyl)hydrazine, in which $R_1$, $R_2$ and $R_4$ are all methyl.

1,2-di-(2'-adamantyl)hydrazine is produced in accordance with the invention by reacting hydrazine with 2-adamantanone to produce di-(2-adamantyl)azine which is converted into the corresponding hydrazine by catalytic hydrogenation. This specific embodiment of the invention is depicted in the following Reaction Scheme IV:

The analogous 1-(1'-adamantyl)-2-(2'-adamantyl)hydrazine can be prepared in a similar way by the reaction of 1-adamantylhydrazine with 2-adamantanone and subsequent hydrogenation of the resulting hydrazone in accordance with Reaction Scheme I described hereinbefore.

By yet another embodiment for the preparation of compounds according to the present invention in which $R_1$ is hydrogen and either of $R_2$ and $R_3$ is an alkanoic acid or ester, a modified method according to the above Reaction Scheme I is used in which one of the nitrogen atoms of the hydrazine is substituted with an esterified alkanoyl group. Examples of esters according to the invention so prepared are the following:

Ethyl [2-(2'-adamantyl)hydrazino]acetate
Ethyl [2-(2'-adamantyl)-1-methylhydrazino]acetate
Ethyl α-[2-(2'-adamantyl)hydrazino]propionate
Ethyl α-[2-(2'-adamantyl)hydrazino]butanoate If desired such compounds may also be isolated as HCl salts.

Also if desired, such an ester may be hydrolyzed under mild conditions to yield a free alkanoic acid. Hydrolysis may, for example, be by ion exchange, using any suitable ion exchanger such as, for example, the one known by the commercial designation "Amberlite 120". This specific embodiment is depicted in the following Reaction Scheme V in which R₄ and R₅ designate alkyl radicals, part (a) showing the formation of an ester, part (b) of an HCl salt and part (c) of a free acid.

Examples of [2-(2'-adamantyl)hydrazino]alkanoic acids according to the invention prepared in this way are:
[2-(2'-adamantyl)hydrazino]acetic acid
[2-(2'-adamantyl)-1-methylhydrazino]acetic acid
α-[2-(2'-adamantyl)hydrazino]propionic acid
α-[2-(2'-adamantyl)hydrazino]butanoic acid Attempts to use in the foregoing embodiment free hydrazino acids as starting materials were in many cases unsuccessful, presumably due to the zwitterion character of such acids by which the nucleophilic character of the hydrazine is destroyed. This, however, does apparently not occur when a hydrazino acid contains a phenyl moiety and in such a case free acid may be used as starting material. For example, α-[1-(2'-adamantyl)-2-methylhydrazino]-α-phenylacetic acid was prepared in accordance with the foregoing embodiment from the free hydrazino acid.

Where in any compound according to the present invention obtained in accordance with any of the foregoing methods a free hydrogen atom of the hydrazine moiety is to be substituted, such substitution may be effected in accordance with known methods, e.g. alkylation with suitable alkylating agents such as treatment with a mixture of sodium hydride and alkyl iodide. For example, 1-(2'-adamantyl)-2-(m-trifluoromethylphenyl)hydrazine obtained, e.g. in accordance with Reaction Scheme I, yields upon treatment with sodium hydride and methyl iodide the corresponding 1-(2'-adamantyl)-2-methyl-2-(m-trifluoromethylphenyl)hydrazine. In this particular case the existing aryl group is responsible for directing the further substitution to the aryl bearing nitrogen atom.

Furthermore, alkylation of any compound according to the present invention in which one hydrazine nitrogen is unsubstituted may also be accomplished by condensing said adamantylhydrazine with a suitable aldehyde or ketone. The resulting hydrazone may be reduced by any of the classical reduction methods employed in Reaction Scheme I.

For example, 2-adamantylhydrazine obtained, e.g. in accordance with Scheme II(a), yields upon treatment with acetone, and subsequent reduction with sodium cyanoborohydride, the corresponding 1-(2'-adamantyl)-2-isopropylhydrazine. Such an embodiment is shown in Reaction Scheme VI where $R_1$ has the same meaning as in formula A and $R_2$ may be H or alkyl and $R_3$ may be alkyl.

A further modification of the aforementioned alkylation-reduction procedure employs an α,ω-dicarbonyl compound, e.g. a dialdehyde, to accomplish a reductive dialkylation to form a new ring including the previously unsubstituted nitrogen of an adamantylhydrazine. According to this method, the dialkylation is accomplished in the presence of a reducing agent, e.g. sodium cyanoborohydride. This modification is shown in Reaction Scheme VII. For example, a solution of 1-(2'-adamantyl)-1-methylhydrazine hydrochloride, e.g. in acetonitrile, was treated with an aqueous solution of glutaric dialdehyde in the presence of sodium cyanoborohydride to give 1-[(2'-adamantyl)methylamino]piperidine. (See Scheme VII, R=CH₃, n=3).

-continued
Reaction Scheme VII

Quite generally, compounds according to the invention in which the hydrazine moiety is monosubstituted may be converted into di-substituted compounds where the substitution is either on the same nitrogen atom or on different nitrogen atoms and any compound according to the invention in which the hydrazine moiety is di-substituted may be converted by further substitution into the corresponding compound in which the hydrazine moiety is tri-substituted.

In the methods of preparation described hereinbefore the compounds according to the invention are obtained other in the free base form or as acid addition salts. Where a free base is obtained it can be converted into an acid addition salt by reaction with a pharmaceutically acceptable acid as known per se and conversely, where the product first obtained is an acid addition salt and the free base is desired the salt is converted into the free base by reaction with a base, again as known per se. Furthermore, it is possible to convert an acid addition salt of a compound of formula A into a different acid addition salt.

Novel compounds according to the invention of the general formula A possess valuable antifungal (human and plant) antiviral, antiprotozoal and antimicrobial properties. Compounds according to the invention are also active against infections caused by such viruses as vaccina, herpes simplex or influenza or by protozan parasites such as leishmania and trypanosoma, or by microorganisms such as leptospira, and alsop possess central nervous system (CNS) activity.

For administration to patients the novel compounds according to the invention are compounded with pharmaceutically acceptable carriers and, if desired, with other pharmaceutically active substances and/or pharmaceutically conventional adjuvants.

The invention also provides compositions containing each as active ingredient a compound of formula A together with an acceptable carrier. Where such compositions are pharmaceutical the carrier must be pharmaceutically acceptable. In case of veterinary compositions or compositions for agricultural use the carriers are selected accordingly.

The invention is further illustrated by the following Examples to which it is not limited, all temperatures being in centigrade.

EXAMPLE 1

1-(2'-Adamantyl)-2,2-dimethylhydrazine hydrochloride

An ethanolic solution of 2.0 g (13 mmol) of 2-adamantanone and 2.0 g (43 mmol) of 1,1-dimethylhydrazine was refluxed for 2½ hrs. The solvent was removed in vacuo and the resulting hydrazone was reduced with 340 mg (8 mmol) of lithium aluminum hydride in 100 ml of refluxing tetrahydrofuran for 16 hrs.

After cooling to room temperature the reaction was quenched with water and extracted 2 times with diethyl ether. The combined organic layers were dried over magnesium sulfate and the title compound was isolated as the hydrochloride salt (1.1 g, 33% yield) and recrystallized from methanol/ether,
mp. 296°–8° (d).
nmr. $(D_2O) \delta 3.13$ (s, 6H).
Anal calcd for $C_{12}H_{23}ClN_2$:C, 62.47; H, 9.98; N, 12.14; Cl, 15.40. Found: C, 62.59; H, 10.22; N, 11.80; Cl, 15.54.

Compounds described in the following examples 2–17, and 41–48 were prepared by the same method as in Example 1, except that equimolar amounts of the appropriate hydrazine derivatives were used.

EXAMPLE 2

1-(2'-Adamantyl)-2-phenethylhydrazine hydrochloride

The title compound was obtained in 20% yield by using phenethylhydrazine instead of 1,1-dimethylhydrazine as in Example 1.
mp. 248°–250° (d), (isopropanol)
nmr. (TFA) $\delta$ 3.46-3.90 (t, 2H); 2.96-3.33 (t, 2H)
Anal calcd for $C_{18}H_{27}ClN_2$: C, 70.47; H, 8.80; N, 9.13; Cl, 11.58. Found: C, 70.14, H, 8.74; N, 9.13; Cl, 11.88.

EXAMPLE 3

1-(2'-Adamantyl)-2-phenylhydrazine hydrochloride

The title compound was obtained in 56% yield by using phenylhydrazine instead of 1,1-dimethylhydrazine as in Example 1.
mp. 230°–234° (d), (isopropanol).
Anal calcd for $C_{16}H_{23}ClN_2$: N, 10.05; Cl, 12.74.
Found: N, 10.00; Cl, 13.22.

EXAMPLE 4

2-(2'-Adamantyl)-1-benzyl-1--phenylhydrazine hydrochloride

The title compound was obtained in 42% yield by using 1-benzyl-1-phenylhydrazine instead of 1,1-dimethylhydrazine as in Example 1.
mp. 208°–9° (d), (isopropanol).
nmr. $(CDCl_3)$ $\delta$ 7.16-8.00 (m, 10H); 5.20 (s, 2H).
Anal calcd for: $C_{23}H_{29}ClN_2$: C, 74.89; H, 7.86; N, 7.56; Cl, 9.60. Found: C, 74.90; H, 8.00; N, 7.61; Cl, 10.07.

EXAMPLE 5

1-(2'-Adamantyl)-2,2-diphenylhydrazine hydrochloride

The title compound was obtained in 65% yield by using 1,1-diphenylhydrazine instead of 1,1-dimethylhydrazine as in Example 1.
mp. 148°–150° (d), (isopropanol).
nmr. $(CDCl_3)$ $\delta$ 6.80-7.60 (m, 10H).
Anal calcd for: $C_{22}H_{27}ClN_2$: C, 74.47; H, 7.61; N, 7.81; Cl, 10.01. Found: C, 74.66; H, 7.82; N, 7.89; Cl, 9.59.

EXAMPLE 6

1-(2'-Adamantyl)-2-(m-trifluoromethylphenyl)hydrazine hydrochloride

The title compound was obtained in 61% yield by using (m-trifluoromethylphenyl)hydrazine instead of 1,1-dimethylhydrazine as in Example 1.
mp. 246°–7° (d), (diethylether).
nmr. $(DMSO-d_6, D_2O)$ $\delta 7.23$-7.63 (m, 4H).
Anal calcd for $C_{17}H_{22}ClF_3N_2$:C, 58.87; H, 6.37; N, 8.07; F, 16.45; Cl, 10.24. Found: C, 59.06; H, 6.65; N, 7.73; F, 16.59; Cl, 10.67.

EXAMPLE 7

1-(2'-Adamantyl)-2-(o-carboxyphenyl)hydrazine

The title compound was obtained in 66% yield by using N-aminoanthranilic acid instead of 1,1-dimethylhydrazine as in Example 1, except that the resulting hydrazone was reduced with sodium cyanoborohydride.

The title compound was isolated as the free base.
mp. 217°–218° (d), (isopropanol).
nmr. (TFA) δ 8.16-8.46 (m, 2H); 7.13-7.50 (m, 2H).
Anal calcd for $C_{17}H_{22}N_2O_2$: C, 71.32; H, 7.69; N, 9.79. Found: C, 70.95; H, 7.86; N, 9.77.

EXAMPLE 8

1-(2'-Adamantyl)-2-(2''-pyridyl)hydrazine hydrochloride

The title compound was obtained in 75% yield by using (2-pyridyl)hydrazine instead of 1,1-dimethylhydrazine as in Example 1.
mp. 248°–250° (d), (ethylacetate/methanol).
nmr. ($CDCl_3$) δ 10.34 (br.s 1H); 6.59-8.07 (m, 4H).
Anal calcd for $C_{15}H_{22}ClN_3$: C, 64.40; H, 7.87; N, 15.02; Cl, 12.70. Found: C, 64.14; H, 7.94; N, 15.01; Cl, 12.98.

EXAMPLE 9

1-(2'-Adamantylamino)pyrrolidine hydrochloride

The title compound was obtained in 58% yield by using 1-aminopyrrolidine instead of 1,1-dimethylhydrazine as in Example 1.
mp 275°–278° (d), (isopropanol).
nmr ($CDCl_3$/TFA) δ 3.46-3.96 (m, 4H).
Anal calcd for $C_{14}H_{25}N_2Cl$: N, 10.91; Cl, 13.84. Found: N, 10.85; Cl, 13.59.

EXAMPLE 10

1-(2'-Adamantylamino)piperidine hydrochloride

The title compound was obtained in 51% yield by using 1-aminopiperidine instead of 1,1-dimethylhydrazine as in Example 1.
mp. 275°–7° (d), (isopropanol).
nmr. ($CDCl_3$/TFA) δ 3.10-3.45 (m, 4H).
Anal calcd for $C_{15}H_{27}ClN_2$: C, 66.54; H, 9.98; N, 10.35; Cl, 13.12. Found: C, 66.39; H, 10.18; N, 10.51; Cl, 13.05.

EXAMPLE 11

1-(2'-Adamantylamino)homopiperidine hydrochloride

The title compound was obtained in 40% yield by using 1-aminohomopiperidine instead of 1,1-dimethylhydrazine as in Example 1.
mp. 268°–271° (d), (isopropanol).
nmr. ($CDCl_3$/TFA) δ 3.23-3.63 (m, 5H).
Anal calcd for $C_{16}H_{29}ClN_2$: C, 67.48; H, 10.19; N, 9.84; Cl, 12.47. Found: C, 67.54; H, 10.26; N, 9.94; Cl, 12.65.

EXAMPLE 12

4-(2'-Adamantylamino)morpholine hydrochloride

The title compound was obtained in 51% yield by using 4-aminomorpholine instead of 1,1-dimethylhydrazine as in Example 1.
mp. 272°–5° (d), (isopropanol).
nmr. ($CDCl_3$/TFA) δ 3.70-4.06 (m, 4H); 3.36-3.70 (m, 4H).
Anal calcd for $C_{14}H_{25}N_2ClO$: C, 61.65; H, 9.17; N, 10.27; Cl, 13.02. Found: C, 61.92; H, 9.09; N, 10.18; Cl, 13.42.

EXAMPLE 13

4-(2'-Adamantylamino)-thiomorpholine-1,1-dioxide hydrochloride hemi-hydrate

The title compound was obtained in 6% yield by using 4-amino-thiomorpholine-1,1-dioxide instead of 1,1-diethylhydrazine as in Example 1.
mp. 285°–290° (d), (dimethylformamide/water).
mass spectrum $(^m/_e)M^+ = 284$.

EXAMPLE 14

1-(2'-Adamantylamino)piperazine hydrochloride

The title compound was obtained in 5% yield by using 1-aminopiperazine instead of 1,1-dimethylhydrazine as in Example 1.
mp. 312°–314° (d), (isopropanol).
nmr. ($CDCl_3$/TFA) δ 3.3-4.0 (m, 8H).
Anal calcd for $C_{14}H_{27}N_3Cl$: C, 61.65; H, 9.91; N, 15.46; Cl, 13.07. Found: C, 61.58; H, 9.88; N, 15.12; Cl, 13.66.

EXAMPLE 15

1-(2'-Adamantylamino)-4-methylpiperazine dihydrochloride

The title compound was obtained in 22% yield by using 1-amino-4'-methylpiperazine instead of 1,1-dimethylhydrazine as in Example 1.
mp. 279°–284° (d), (isopropanol).
nmr. ($CDCl_3$/TFA) δ 3.50-4.06 (m, 6H); 2.26 (s, 3H).
Anal calcd for $C_{25}H_{29}Cl_2N_3$: C, 55.90; H, 9.00; N, 13.04. Found: C, 55.63; H, 9.27; N, 13.19.

EXAMPLE 16

1-(2'-Adamantylamino)-4-benzylpiperazine dihydrochloridemonohydrate

The title compound was obtained in 15% yield by using 1-amino-4-benzylpiperazine instead of 1.1-dimethylhydrazine as in Example 1.
mp. 269°–273° (d), (isopropanol/methanol).
nmr. ($CDCl_3$/TFA) (s, 5H); 4.00-4.36 (d, 2H).
Anal calcd for $C_{21}H_{35}H_3Cl_2O$: N, 10.09; Cl, 17.06. Found: N, 9.72; Cl, 17.35.

EXAMPLE 17

1-(2'-Adamantylamino)-4-(m-trifluoromethylphenyl)-piperazine hydrochloride

The title compound was obtained in 30% yield by using 1-amino-4-(m-trifluoromethylphenyl)piperazine instead of 1,1-dimethylhydrazine as in Example 1.
mp. 254°–7° (d), (isopropanol).
nmr. ($CDCl_3$/TFA) δ 7.26-8.00 (m, 4H); 3.53-4.23 (m, 8H).
Anal calcd for $C_{21}H_{29}N_3F_3Cl$: C, 60.64; H, 6.97; N, 10.10; F, 13.71; Cl, 8.54. Found: C, 60.93; H, 7.27; N, 10.24; F, 13.42; Cl. 8.91.

EXAMPLE 18

2-Adamantylhydrazine hydrochloride

An ethanolic solution of 34 g (450 mmol) of acetylhydrazine and 68 g (450 mmol) of 2-adamantanone was refluxed for 2 hours, allowed to cool and the white precipitate collected by filtration to give 83 g of acetyl-2-adamantylhydrazone; mp 204°–206°.

Reduction of this hydrazone was accomplished by refluxing 30 g (140 mmol) of the crude product in 400 ml dry tetrahydrofuran, with 5.5 g (140 mmol) of lithium aluminum hydride for 16 hours.

After cooling, the reaction was quenched with water and extracted 2 times with methylene chloride. The combined organic layers were dried with magnesium sulfate. Solvent removal in vacuo yielded 27 g of white solid with spectra consistent with 1-acetyl-2-(2'-adamantyl)hydrazine: mp 177°–9°.

The acetyl group was cleaved by refluxing 10 g of this product in 70 ml of conc. HCl for 2 hours. Upon cooling the precipitate was collected by filtration (7.9 g), and 2-adamantylhydrazine was recrystallized from isopropanol as the HCl salt in 63% yield.

mp. 295°–8° (d).

nmr. (DMSO-$d_6$) δ 7.00 (m, 4H, exchangeable); 3.30 (br.s, 1H), 1.66 (m, 14H).

Anal calcd for $C_{10}H_{19}ClN_2$: C, 59.26; H, 9.38; N, 13.82; Cl, 17.52. Found: C, 59.08; H, 9.54; N, 13.72; Cl, 17.72.

EXAMPLE 19

2-Adamantylhydrazine hydrochloride

The title compound was alternatively prepared in 48% yield by using benzoylhydrazine instead of acetylhydrazine following the procedure of Example 18.

EXAMPLE 20

2-Adamantylhydrazine hydrochloride

The title compound was alternatively prepared in 17% yield using t-butylcarbonate instead of acetylhydrazine following the procedure of Example 18.

The t-butylcarbonate group was ultimately cleaved in nitromethane with hydrogen chloride.

EXAMPLE 21

1-(2'-Adamantyl)-2,2-dimethylhydrazine hydrochloride

To a suspension of 360 mg (9 mmol) of sodium hydride in 75 ml of tetrahydrofuran was added 2.0 g (7.5 mmol) of the hydrazone resulting from the condensation of 1.4 g (9 mmol) of adamantonone and 5.4 g (27 mmol) of tert-butylcarbazate. After 1 hour reflux the rection was cooled and 1.06 g (7.5 mmol) of methyliodide was added and reflux continued an additional 2 hours, at which time the reaction was cooled, quenched with water and extracted 2 times with methylenechloride. The combined organic layers were dried over magnesium sulfate and the solvent removed in vacuo leaving 1.9 g of product with spectra consistent with the expected methylated hydrazone. Reduction of the carbazate as well as the hydrazone moieties was accomplished by treating 850 mg (3 mmol) of this product with 110 mg (3 mmol) of lithium aluminum hydride in 20 ml of refluxing tetrahydrofuran for 16 hours. After cooling the reaction was quenched with aqueous ammonium chloride solution and extracted 2 times with methylene chloride. The combined organic layers were dried over magnesium sulfate and solvent removal in vacuo yielded 450 mg of oil which was dissolved in diethyl ether, and treated with gaseous hydrogen chloride to give the title compound (50% yield) with identical properties to those described in Example 1.

EXAMPLE 22

1-(2'-Adamantyl)-2-ethyl-2-methylhydrazine hydrochloride

The title compound was obtained in 49% yield by using ethyl iodide instead of methyl iodide following the procedure of Example 21.

mp. 281°–4° (d), (isopropanol).

nmr. (CDCl$_3$/TFA) δ 3.43 (q, 2H); 3.06 (s, 3H); 1.45 (t, 3H).

Anal calcd for $C_{13}H_{25}N_2Cl$: C, 63.80; H, 10.22; N, 11.45; Cl, 14.51. Found: C, 63.72; H, 10.29; N, 11.01; Cl, 14.37.

EXAMPLE 23

1-(2'-Adamantyl)-2-ethyl-2-methylhydrazine hydrochloride

To 2.3 g (60 mmol) of sodium hydride in 100 ml of refluxing tetrahydrofuran was added 10 g (48 mmol) of acetyladamantylhydrazone (cf Example 18). After 1 hour the reaction was cooled and 6.8 g (47 mmol) of methyl iodide was added. After an additional 2 hours reflux, the reaction was cooled, quenched with water and extracted 2 times with methylene chloride. The combined organic layers were dried over magnesium sulfate and solvent removal in vacuo yielded 1-(2'-adamantyl)-2-acetyl-2-methylhydrazone.

Treatment of 1.7 g (7.9 mmol) of this intermediate with 360 mg (9.4 mmol) of lithium aluminum hydride in 75 ml of refluxing tetrahydrofuran for 16 hours reduced both the hydrazone and the amide to give the title compound in 70% yield with properties identical to those described in Example 22.

EXAMPLE 24

1-(2'-Adamantyl)-2,2-diethylhydrazine hydrochloride

The title compound was obtained in 44% yield by using ethyl iodide instead of methyl iodide following the procedure of Example 23.

mp. 270°–2° (d), (isopropanol).

nmr. (CDCl$_3$) δ 3.20-3.62 (q, 4H), 1.33-1.66 (t, 6H).

Anal calcd for $C_{14}H_{27}ClN_2$: C, 64.99; H, 10.46; N, 10.85; Cl, 13.75. Found: C, 64.65; H, 10.42; N, 11.20; Cl, 13.82.

EXAMPLE 25

1-(2'-Adamantyl)-2-methylhydrazine hydrochloride

To 2.3 g (60 mmol) of sodium hydride in refluxing tetrahydrofuran was added 10 g (48 mmol) of adamantylacetylhydrazine (cf Example 18). After 1 hour the reaction was cooled, 6.8 g (47 mmol) of methyl iodide added and reflux continued an additional 2 hours, at which time aqueous work-up gave 10 g of crude 1-(2'-adamantyl)-2-methyl-2-acetylhydrazone.

This hydrazone (6.5 g, 29 mmol) was reduced with 200 mg of PtO$_2$.H$_2$O (Adams Catalyst) in 200 ml absolute ethanol under 60 psi H$_2$ for 2 hours. Filtration and evaporation gave 6.2 g of crude material which was immediately refluxed in 45 ml of conc. HCl for 2 hours. Collection of the precipitate upon cooling yielded 4.3 g of the title compound (64% yield).

mp. 305°–307° (d).

nmr. (TFA) δ 3.33 (s, 3H).

Anal calcd for $C_{11}H_{21}ClN_2$: C, 60.96; H, 9.69; N, 12.93; Cl, 16.39. Found: C, 60.91; H, 9.58; N, 12.64; Cl, 16.81.

EXAMPLE 26

1-(2'-Adamantyl)-2-ethylhydrazine hydrochloride

The title compound was obtained in 62% yield by using ethyl iodide instead of methyl iodide according to the procedure of Example 25.

mp. 283°-292°.

nmr. (TFA) δ 3.53 (q, 2H); 1.49 (t, 3H).

Analysis: Calculated for $C_{12}H_{23}ClN_2$: C, 62.47; H, 9.98; N, 12.14; Cl, 15.40. Found: C, 62.33; H, 9.37; N, 11.96; Cl, 15.83.

An additional crystallization raised the mp above 300°.

EXAMPLE 27

1-(2'-Adamantyl)-1-methylhydrazine hydrochloride

To a solution of 1.35 g (5 mmol) of 1-(2-adamantyl)-1-benzoylhydrazine (cf Example 19) in 30 ml of methyl acetate at 0° was added dropwise 570 mg (5.5 mmol) of methyl fluorosulfonate. After 15 min. the volatiles were removed in vacuo and the resulting oil taken up in 50 ml of methylene chloride, washed with equal volumes each of 2N sodium hydroxide and water, and dried to give 1 g of 1-(2'-adamantyl)-2-benzoyl-1-methylhydrazine, a white solid.

The benzoyl group was cleaved by refluxing 1 g of the above intermediate in 50 ml of conc. HCl for 6 hours. Following cooling and extraction with 1:1 benzene/ether the aqueous layer was evaporated to dryness to give 580 mg of the title compound (50% yield).

mp. 199°-202° (d), (isopropanol).

nmr. (CDCl$_3$) δ 3.00 (s, 3H).

Analysis: Calculated for $C_{11}H_{21}ClN_2$: C, 60.97; H, 9.70; N, 12.93; Cl, 16.39. Found: C, 60.68; H, 9.48; N, 12.62; Cl, 16.00.

EXAMPLE 28

1-(2'-Adamantyl)-2-methyl-2-(m-trifluoromethylphenyl)hydrazine hydrochloride

A mixture of 3 g (10 mmol) of 1-(2'-adamantyl)-2-(m-trifluoromethylphenyl)hydrazine (cf Example 6) and 1 g (25 mmol) of sodium hydride in 100 ml of benzene was refluxed for 16 hours. After cooling the reaction to room temperature 7.1 g (50 mmol) of methyl iodide was added and the reaction refluxed an additional 16 hours.

After cooling the reaction was quenched with water and extracted 2 times with methylene chloride. The combined organic layers were dried over magnesium sulfate and solvent removal in vacuo yielded 3.3 g. of crude material which was purified by preparative layer chromatography on silica (cyclohexane: ethylacetate, 7:1), isolating 1.1 g of oil, which was converted to the title compound by treatment with hydrogen chloride (30% yield).

mp. 139°-144° (d), (ether).

nmr. (CDCl$_3$) δ 7.40-8.50 (m, 4H); 3.60 (s, 3H).

Analysis: Calculated for $C_{18}H_{24}N_2ClF_3$: C, 59.92; H, 6.65; N, 7.76; F, 15.81; Cl, 9.84. Found: C, 59.77; H, 6.56; N, 7.58; F, 15.71; Cl, 9.83

EXAMPLE 29

1-(2'-Adamantyl)-2-methyl-2-(m-trifluoromethylphenyl)hydrazine hydrochloride hemihydrate The title compound was prepared in 83% yield by using 1-methyl-1-(m-trifluoromethylphenyl)hydrazine hydrochloride instead of 1,1-dimethylhydrazine as in Example 1, except that the resulting hydrazone was reduced with sodium cyanoborohydride.

mp. 165°-70° (d) (ethylacetate).

nmr. (CDCl$_3$) δ 7.40-850 (m, 4H);3.60 (s, 3H).

Analysis; Calculated for $C_{10}H_{25}N_2ClF_3O_{\frac{1}{2}}$: C, 58.45; H, 6.76; N, 7.58; F, 15.42; Cl, 9.85. Found: C, 58.84; H, 6.44; N, 7.58; F, 14.93; Cl 9.83.

EXAMPLE 30

1,2-Di-(2'-adamantyl)hydrazine 1.1 g (3.8 mmol) of di-(2-adamantyl) azine was reduced with 60 mg PtO$_2$.H$_2$O (Adams Catalyst) in 30 ml methanol under 60 psi H$_2$ for 16 hours giving 790 mg of the title compound (72% yield).

mp. 326°-9° (methanol/methylene chloride).

Analysis: Calculated for $C_{20}H_{32}N_2$: C, 79.94; H, 10.66; N, 9.32. Found: C, 79.77; H, 10.49; N, 9.31.

EXAMPLE 31

1-(1'-Adamantyl)-2-(2''-adamantyl)hydrazine hydrochloride

An ethanolic solution of 1.5 g (10 mmol) of 2-adamantanone and 2.3 g (10 mmol) of 1-adamantylhydrazine hydrochloride was refluxed for 3 hours. After cooling, evaporation of solvent was followed by an aqueous basic work up to give 2.5 g of the hydrazone which was reduced with 250 mg of PtO$_2$.H$_2$O in 200 ml absolute ethanol for 3 hours under 60 psi H$_2$.

After removal of solvent in vacuo, the residue was suspended in ether, filtered, and the filtrate treated with HCl. The title compound was obtained in 45% yield.

mp. >300° (methylene chloride/ether).

nmr. (CDCl$_3$/TFA) δ 3.2 (m, 1H); 1.6-2.5 (m, 29H).

Anal calcd for $C_{20}H_{33}N_2Cl$: C, 71.28; H, 9.88; N, 8.32. Found: C, 70.84; H, 9.12; N, 8.21.

EXAMPLE 32

Ethyl [2-(2'-adamantyl)hydrazino]acetate hydrochloride

An ethanolic solution of 1 g (6.6 mmol) of adamantanone and 1 g (6.6 mmol) of ethyl hydrazinoacetate hydrochloride was refluxed for 2 hours. After cooling, the solvent was removed in vacuo and the resulting white solid neutralized with aqueous sodium carbonate and extracted 2 times with methylene chloride. The combined organic layers were dried over magnesium sulfate and solvent removal yielded 1.2 g of oil with spectra consistent with the expected hydrazone which was immediately reduced with 200 mg of PtO$_2$.H$_2$O (Adams Catalyst) in 50 ml absolute ethanol at 60 psi H$_2$ for 16 hours. After filtration and solvent removal in vacuo, the resulting oil was dissolved in ether and treated with gaseous hydrogen chloride to give 800 mg (50%) of the title compound.

mp. 201° (d), (isopropanol).

nmr. (CDCl$_3$) δ 4.3 (q, 2H), 4.2 (s, 2H), 1.3 (t, 3H).

Anal calcd for $C_{14}H_{25}ClN_2O_2$: C, 58.23; H, 8.68; N, 9.72; Cl, 12.32. Found: C, 58.07; H, 8.57; N, 9.71; Cl, 12.70.

The compounds described in the following Examples 33-35 were prepared by the same method as in Example 32, with the noted exceptions and using the appropriate hydrazine derivatives.

EXAMPLE 33

Ethyl [2-(2'-adamantyl)-1-methylhydrazino]acetate hydrochloride

The title compound was obtained in 65% yield by using ethyl 1-methylhydrazinoacetate instead of ethyl hydrazinoacetate hydrochloride and reducing for 48 hours instead of 16 hours as in Example 32.

mp. 164°–5° (d), (ethyl acetate).

Anal calcd for $C_{15}H_{27}ClN_2O_2$: C, 59.50; H, 8.92; N, 9.26; Cl, 11.73. Found: C, 59.41; H, 8.76; N, 9.02; Cl, 11.41.

EXAMPLE 34

Ethyl α-[2-(2'-adamantyl)hydrazino]propionate hydrochloride

The title compound was obtained in 45% yield by using ethyl hydrazino-2-propionate hydrochloride instead of ethyl hydrazinoacetate hydrochloride as in Example 33.

mp. 215°–217° (d), (isopropanol).

Anal calcd for $C_{15}H_{27}ClN_2O_2$: C, 59.50; H, 8.92; N, 9.26; Cl, 11.73. Found: C, 59.57; H, 8.95; N, 9.21; Cl, 12.13

EXAMPLE 35

Ethyl α-[2-(2'-adamantyl)hydrazino]butanoate hydrochloride

The title compound was obtained in 65% yield by using ethyl hydrazino-2-butanoate hydrochloride instead of ethyl hydrazinoacetate hydrochloride.

mp. 194°–7° (d), (ethyl acetate/ether).

Anal calcd for $C_{16}H_{29}ClN_2O_2$: C, 60.66; H, 9.16; N, 8.84; Cl, 11.21. Found: C, 60.88; H, 9.38; N, 9.05; Cl, 11.35.

EXAMPLE 36

[2-(2'-adamantyl)hydrazino]acetic acid hydrochloride

The hydrazino ester hydrochloride (1 g) of Example 32 was hydrolyzed with 4 g of Amberlite IR-120 (H) ion exchange resin in 50 ml of refluxing water for 16 hours to give the title compound in 47% yield upon filtration and evaporation of solvent.

mp. 184°–5° (d), (isopropanol).

nmr. (TFA) δ 4.20 (s, 2H).

Anal Calcd for $C_{12}H_{21}N_2O_2Cl$: C, 55.27; H, 8.06; N, 10.74; Cl, 13.62. Found: C, 55.65; H, 8.53; N, 10.90; Cl, 13.51.

EXAMPLE 37

[2-(2'-Adamantyl)-1-methylhydrazino]acetic acid hydrochloride

The hydrazino ester hydrochloride of example 33 (6 g) was hydrolyzed with 3 g of Amberlite IR-120 (H) for 6 hours in refluxing water to give the title compound in 57% yield after filtration and evaporation of solvent.

mp. 190°–3° (d), (isopropanol).

nmr. (TFA) δ 6.33 (s, 2H), 3.28 (s, 3H).

Anal calcd for $C_{13}H_{23}N_2ClO_2$: C, 56.83; H, 8.34; N, 10.16; Cl, 12.88. Found: C, 56.38; H, 8.47; N, 9.94; Cl, 13.02.

EXAMPLE 38

α-[2-(2'-Adamantyl)hydrazino]propionic acid hydrochloride

The hydrazino ester hydrochloride of Example 34 (4.7 g) was hydrolyzed with 5 g of Amberlite IR-120 (H) for 16 hours in refluxing water to give the title compound in 60% yield after filtration and evaporation of solvent.

mp. 183°–6° (d), (isopropanol/ether).

Anal calcd for $C_{13}H_{23}N_2O_2Cl$: C, 56.83; H, 8.38; N, 10.20; Cl, 12.93. Found: C, 56.48; H, 8.77; N, 9.95; Cl, 12.64.

EXAMPLE 39

α-[2-(2'-Adamantyl)hydrazino]butanoic acid hydrochloride

The hydrazino ester hydrochloride of Example 35 (5 g) was hydrolyzed with 2.5 g of Amberlite IR-120 (H) in refluxing water for 16 hrs to give the title compound in 20% yield after filtration and evaporation of solvent.

mp. 205°–8° (d), (isopropanol).

Anal calcd for $C_{14}H_{25}N_2O_2Cl$: C, 58.23; H, 8.66; N, 9.70; Cl, 12.30. Found: C, 58.27; H, 8.60; N, 9.46; Cl, 12.21.

EXAMPLE 40

α-[1-(2'-Adamantyl)-2-methylhydrazino]-α-phenylacetic acid

The title compound was obtained in 58% yield by using hydrazinophenylacetic acid hydrochloride instead of 1,1-dimethylhydrazine following the procedure of Example 1, except that the resulting hydrazone was reduced with sodium cyanoborohydride.

mp. 134°–7° (isopropanol).

nmr. ($CDCl_3$) δ 7.06–7.53 (m, 5H); 4.31 (S, 1H), 2.36 (S, 3H).

Anal calcd for $C_{19}H_{26}N_2O_2$: C, 72.61; H, 8.28; N, 8.91. Found: C, 72.74; H, 8.42; N, 8.91.

EXAMPLE 41

1-(2'-Adamantyl)-2-[1''-(2'''-hydroxyethyl)]hydrazine hydrochloride

The title compound was obtained in 36% yield by using 2-hydrazinoethanol instead of 1,1-dimethylhydrazine as in Example 1, except that the resulting hydrazone was reduced with 50 psi $H_2$ over 10% palladium on carbon.

mp. 220° (d), (ethylacetate/methanol).

nmr. ($CDCl_3$) δ 3.9 (m, 2H); 3.45 (m, 3H).

Anal calcd for $C_{12}H_{23}N_2OCl$: C, 58.41; H, 9.33; N, 11.35. Found: C, 58.07; H, 9.29; N, 11.52.

EXAMPLE 42

1-(2'-Adamantyl)-2-butylhydrazine hydrochloride

The title compound was obtained in 15% yield by using butylhydrazine oxalate instead of 1,1-dimethylhydrazine as in Example 1 except that the resulting hydrazone was reduced in sodium cyanoborohydride.

mp. 230° (d), (isopropanol).

nmr. ($CDCl_3$) δ 0.95 (t, 3H).

Anal calcd for $C_{14}H_{27}N_2Cl$: N, 10.83. Found: N, 10.69.

EXAMPLE 43

1-(2'-Adamantyl)-2-(adamant-1''-ylmethyl)hydrazine hydrochloride

The title compound was obtained in 46% yield by using adamant-1-ylmethylhydrazine instead of 1,1-dimethylhydrazine as in Example 1, except that the resulting hydrazone was reduced with sodium cyanoborohydride.

mp >300° (methanol).
nmr. (CDCl$_3$/TFA): δ 3.4 (m, 1H); 2.7 (m, 2H).
Anal calcd for C$_{21}$H$_{35}$N$_2$Cl: N, 7.98. Found: N, 7.87.

EXAMPLE 44

1-(2'-Adamantyl)-2-(p-bromophenyl)hydrazine hydrochloride

The title compound was obtained in 17% yield by using p-bromophenylhydrazine instead of 1,1-dimethylhydrazine as in Example 1.

mp. 204°-7° (d), (isopropanol).
nmr. (CDCl$_3$/TFA) δ 6.7-7.3 (m, 4H), 4.5 (br. s. 1H).
Anal calcd for C$_{16}$H$_{22}$N$_2$ClBr: C, 53.70; H, 6.15; N, 7.83. Found: C, 52.41; H, 6.21; N, 7.65.

EXAMPLE 45

1,(2'-Adamantyl-2-[4''-(7'-chloroquinolinyl)]hydrazine hydrochloride hydrate

The title compound was obtained in 40% yield by using 7-chloro-4-hydrazinoquinoline instead of 1,1-dimethylhydrazine as in Example 1, except that the resulting hydrazone was reduced with sodium cyanoborohydride.

mp. 286°-288° (d), (isopropanol).
nmr. (CDCl$_3$/TFA) δ 7.2-8.5 (m, 5H); 3.3 (m, 1H).
Anal calcd for C$_{19}$H$_{25}$N$_3$Cl$_2$O: C, 59.69; H, 6.59; N, 10.99; Cl, 18.58. Found: C, 59.95; H, 6.29; N, 11.29; Cl, 18.99.

EXAMPLE 46

1-(2'-Adamantylamino)heptamethyleneimine hydrochloride

The title compound was obtained in 24% yield by using 1-aminoheptamethyleneimine instead of 1,1-dimethylhydrazine as in Example 1.

mp. 247°-250° (d), (isopropanol/ethyl acetate).
nmr. (CDCl$_3$) δ 3.4 (br.s., 4H).
Anal calcd for C$_{17}$H$_{31}$N$_2$Cl: C, 68.34; H, 10.38; N, 9.38; Cl, 11.89. Found: C, 68.09, H, 10.49; N, 9.49; Cl, 12.17

EXAMPLE 47

4-(2'-Adamantylamino)thiomorpholine hydrochloride

The title compound was prepared in 35% yield by using 4-aminothiomorpholine instead of 1,1-dimethylhydrazine as in Example 1.

mp. 257°-261° (d), (isopropanol).
nmr. (CDCl$_3$/TFA) δ 3.3-3.7 (m, 4H), 2.7-3.0 (m, 4H).
Anal calcd for C$_{14}$H$_{25}$N$_2$Cl S: C, 58.23; H, 8.66; N, 9.70; Cl, 12.30; S, 11.08. Found: C, 58.50; H, 8.62; N, 9.65; Cl, 12.72; S, 10.96.

EXAMPLE 48

1-(2'-Adamantylamino)hydantoin hydrochloride

The title compound was obtained in 65% yield by using 1-aminohydantoin sulfate instead of 1,1-dimethylhydrazine as in Example 1 except that the resulting hydrazone was reduced with sodium cyanoborohydride.

mp. 210°-213° (d), (isopropanol/methanol).
nmr. (CDCl$_3$/TFA) δ 4.6 (s, 2H).
Anal calcd for C$_{13}$H$_{20}$N$_3$O$_2$Cl: C, 54.64; H, 7.00; N, 14.71; Cl, 12.43. Found: C, 54.37; H, 7.12; N, 14.77; Cl, 12.15.

EXAMPLE 49

1-(2'-Adamantyl)-1,2-dimethylhydrazine hydrochloride

To a solution of 10 g (45 mmol) of 1-(2'-adamantyl)-2-acetyl-2-methylhydrazine (cf Example 25) in 300 ml of methyl acetate (under nitrogen) was added 5.1 g (45 mmol) of methyl fluorosulfonate over ½ hr. After 2 hrs stirring the volatiles were removed in vacuo and the residue partitioned between saturated aqueous sodium bicarbonate and chloroform. The organic layer was dried and concentrated to 9 g 1-(2'-adamantyl)-1,2-dimethyl-2-acetylhydrazine which was hydrolyzed in 60 ml conc. HCl for 2 hrs. After removal of the volatiles in vacuo, the residue was crystallized from isopropanol to give title compound in 15% yield.

mp. 189°-191° (d), (isopropanol).
nmr. (CDCl$_3$/TFA) δ 2.9 (s, 3H), 2.7 (s, 3H).
Anal calcd for C$_{12}$H$_{23}$N$_2$Cl: C, 62.47; H, 9.97; N, 12.14; Cl, 15.40. Found: C, 62.52; H, 9.86; N, 11.89; Cl, 15.27.

EXAMPLE 50

1-(2'-Adamantyl)-1,2-dimethyl-2-ethylhydrazine hydrochloride

To 5.3 g (25 mmol) of 1-(2'-adamantyl)-2-acetylhydrazine (cf Example 18) in 50 ml of methyl acetate at 0° was added 3.1 g (25 mmol) of methyl fluorosulfonate with stirring. After 1 hr the volatiles were removed in vacuo and the residue partitioned between 10% of NaOH and methylene chloride. The dried organic phase was concentrated to 5 g (22 mmol) 1-(2'-adamantyl)-1-methyl-2-acetylhydrazine which was reacted with 1.1 g of NaH (25 mmol, 55% mineral oil dispersion) in 100 ml of dry tetrahydrofuran. After 2 hrs of reflux, the suspension was allowed to cool to room temperature and 3.1 g (21 mmol) of methyl iodide was added. After an additional 2 hrs of reflux the reaction was cooled and quenched with water. The mixture was then partitioned between water and methylene chloride and the dried organic layer concentrated to 4.4 g (19 mmol) 1-(2'-adamantyl)-1,2-dimethyl-2-acetylhydrazine which was treated with 1.3 g (34 mmol) of lithium aluminum hydride in dry tetrahydrofuran. After 3 hrs reflux the reaction was cooled to 0° and the reaction was quenched with an excess of sodium sulfate decahydrate. After filtration, the concentrated filtrate was dissolved in ether and treated with gaseous HCl to give the title compound in 21% overall yield.

mp. 170° (d), (isopropanol).
nmr. (CDCl$_3$) δ 2.76 (m, 5H); 2.48 (s, 3H).
Anal calcd for C$_{14}$H$_{27}$N$_2$Cl: N, 10.83. Found: N, 10.47.

EXAMPLE 51

1-(2'-Adamantyl)-2-isopropylhydrazine hydrochloride

A methanolic solution of 2.5 g (12.3 mmol) of 2-adamantylhydrazine hydrochloride and 2 g (34 mmol) of acetone was refluxed for 4 hrs. The resulting hydrazone was reduced with sodium cyanoborohydride in ethanol. After 1 hr. the suspension was neutralized with 10% NaOH, the volatiles removed in vacuo and the residue partitioned between ether and water. The dried ether layer was treated with gaseous HCl. The title compound was obtained in 26% yield.

mp. >315° (isopropanol).

nmr. (CDCl$_3$/TFA) δ 3.1-3.7 (m, 2H); 1.4 (d, 2H).

Anal calcd for $C_{13}H_{25}N_2Cl$: N, 11.44; Cl, 14.51. Found: N, 11.18; Cl, 14.21.

EXAMPLE 52

1-[(2'-Adamantyl)methylamino]piperidine hydrochloride hydrate

To a solution of 1.1 g (5 mmol) of 1-(2-adamantyl)-1-methylhydrazine hydrochloride (cf Example 27) in 15 ml of acetonitrile was added 3 g (7.5 mmol) of a 25% aqueous solution of glutaric dialdehyde followed by 800 mg (12.5 mmol) of sodium cyanoborohydride and a few drops of conc. HCl to ensure acidity. After 3 hrs. of stirring the volatiles were removed in vacuo and the residue partitioned between 10% KOH and methylene chloride. The organic layer was dried (MgSO$_4$) and the solvent removed in vacuo and replaced by diethyl ether. The resulting solution was treated with HCl to form the title compound which was isolated in 45% yield by filtration and washed with ethyl acetate.

mp. 195°-201° (d), (ethyl acetate wash).

nmr. (CDCl$_3$) δ 3.8-2.8 (m, 4H), 2.9 (s, 3H).

Anal calcd for $C_{16}H_{31}N_2ClO$: C, 63.47; H, 10.25; N, 9.26; Cl, 11.74. Found: C, 63.64; H, 10.45; N, 9.18; Cl, 11.96.

In the following test results are given which demonstrate the antimicrobial, antiprotozoan, CNS, antifungal and antiviral activities of compounds according to the invention.

Antimicrobial activity was demonstrated on Leptospira and mycoplasma; antiprotozoan activity on Leishmania and Trypanosoma; CNS activity on albino rats and albino mice; antifungal activity on plant fungi; and antiviral activity on HSV-1 (Herpes Simplex) and on influenza virus. The following are the results.

ANTI LEPTOSPIRAL ACTIVITY

The tests were carried out under the following conditions:

Leptospira: Leptospira canicola Kipod 146
Inoculum: 1-10$^5$ cells/ml
Incubation time: 10 days, 28° C.
Evaluation: Direct count in dark field microscopy after 4, 7 and 10 days.
Media used:
1 Minimal
2 Minimal +0.5% albumin (Pentex)
3 Korthof rich medium with 8% serum.
4 Korthof rich medium with 2% serum.
Results are summarized in the following table:

ANTI LEPTOSPIRAL ACTIVITY

| Compound of Example No. | Solubility | Minimal inhibition concentration (μg/ml) | | | |
|---|---|---|---|---|---|
| | | minimal | minimal + Pentex | Korthof + 8% | Korthof + 2% |
| 1 | Water | 12.5 | 12.5 | 12.5 | |
| 10 | Water | 12.5 | | 100 | |
| 18 | Water | 3.125 | 6.25 | 125 | 12.5 |
| 27 | Water | 3.125 | 6.25 | 50 | |
| 37 | Water | 25 | 25 | 12.5-25 | 12.5 |
| 3 | DMSO | 6.25 | | 100 | |
| 6 | DMSO | 12.5 | | 50 | |
| 29 | DMSO | 6.25 | | 6.25 | |

It is seen from the above results that the tested compounds of Examples Nos. 1, 3, 6, 10, 18, 27, 29 and 37 were all found to be active.

ANTIMYCOPLASMA ACTIVITY

Some of the compounds were tested against 4 mycoplasma. The method used was as follows:
Microorganisms:
1. M. gallisepticum
2. M. capricolum
3. M. hominis
4. A. laidlawii
Assay:
50% inhibition of growth in liquid medium.
Results:

The tested compounds of Examples Nos. 2, 10, 16 were found to show a 50% inhibition in concentrations between 5-30 μg/ml, which are within the range of antibiotic activity.

ANTI LEISHMANIA AND ANTI TRYPANOSOMA TESTS

A. Scoring of drug activity

1. L. tropica
  a. amastigotes in peritoneal exudate cells in Mc Coy's medium in vitro at 37° C.
    +++ = clearance of all parasites in 24 hours
    ++ = clearance of all parasites in 48 hours
    + = clearance of all parasites in 72 hours
    ± = Partial clearance of parasites in 72 hours or more
    − = No activity against parasites.
  b. promastigotes in Mc Coy's medium in vitro at 27° C.
    +++ = No viable parasites after 24 hours
    ++ = No viable parasites after 48 hours
    + = No viable parasites after 72 hours
    ± = No viable parasites after 96 hours p2 − − = viable parasites after 120 hours.
11. Trypanosoma in vitro
  Trypanosoma in RPM1 medium in vitro at 37° C. Scoring as in b.

ANTI LEISHMANIA AND ANTI TRYPANOSOMA TESTS

| Compound of Example No. | Results: | | | | | |
|---|---|---|---|---|---|---|
| | Leishmania | | | | Trypanosoma in vitro | |
| | Amastigote | | Promastigote | | | |
| | 10μg | 100μg | 10μg | 100μg | 10μg | 100μg |
| 3 | | | | | + | +++ |
| 8 | + | +++ | | | + | +++* |
| 11 | | | | | + | +++** |
| 16 | − | − | +++ | +++* | | |

ANTI LEISHMANIA AND ANTI TRYPANOSOMA TESTS -continued

| Compound of Example No. | Results: | | | | | |
|---|---|---|---|---|---|---|
| | Leishmania | | | | Trypanosoma in vitro | |
| | Amastigote | | Promastigote | | | |
| | 10μg | 100μg | 10μg | 100μg | 10μg | 100μg |
| 18 | ++ | +++ | — | — | | |
| 25 | — | ++ | — | +++ | | |
| 27 | ± | ++ | — | +++ | | |
| 36 | — | ++ | — | ++ | | |
| 38 | — | ++ | ± | ++ | | |
| 49 | | | | | — | ++ |
| 51 | ± | ++ | | | — | +++ |
| Control Pentamidine | | +++ | +++ | | — | ++ |

*An effect was observed with this drug after 1 h at this concentration. No effect was observed with Pentamidine at this time.
**Slight effect.

Summary

The tested compounds of Examples Nos. 8, 16, 18, 25, 27, 36, 38, 51 were found to be active against Leishmania.

The tested compounds of Examples Nos. 3, 8, 11, 49, 51 were found to be active against Trypanosoma.

ANTIPARKINSON ACTIVITY

Male Charles River albino rats, weighing 200–250 g, were used. Catalepsy was produced by haloperidol, 5 mg/kg i.p. The animals were placed with their front paws on a horizontal bar, about 10 cm above the ground, and animals were considered cataleptic if not changing posture for at least 30 sec. Cataleptic animals were injected i.p. with one of the drugs at a dose of 40–80 mg/kg. Catalepsy was estimated again at the intervals indicated.

Drug: Control Symmetrel, Route, I.P., Dose: 80 mg/kg

| Time | rat 1 | rat 2 | rat 3 | rat 4 | rat 5 |
|---|---|---|---|---|---|
| 0 | + | + | + | + | + |
| 45 | + | — | — | — | — |
| 90 | + | — | + | + | — |
| 110 | + | + | — | — | — |
| 180 | + | + | — | — | + |
| anticataleptic effect | 0/4 | 2/4 | 3/4 | 3/4 | 3/4 |
| Mean Maximal effect 2.2/4 | | | | | |

Drug: Compound of Example 27, Route: i.p.
Dose: 80 mg/kg

| Time | rat 1 | rat 2 | rat 3 | rat 4 | rat 5 |
|---|---|---|---|---|---|
| 0 | + | + | + | + | + |
| 45 | — | + | — | + | — |
| 90 | — | + | — | — | — |
| 110 | — | — | + | — | — |
| 180 | + | + | + | — | — |
| anticataleptic effect | 3/4 | 1/4 | 2/4 | 3/4 | 4/4 |
| Date 1/3/78 | Mean maximal effect 2.6/4 | | | | |

Drug: Compound of Example 36, Route: i.p.
Dose: 80 mg/kg

| Time | rat 1 | rat 2 | rat 3 | rat 4 | rat 5 |
|---|---|---|---|---|---|
| 0 | + | + | + | + | + |
| 45 | — | + | — | — | + |
| 90 | — | — | — | — | + |
| 110 | + | + | — | + | + |
| 180 | + | + | + | + | + |
| anticataleptic effect | 2/4 | 1/4 | 3/4 | 2/4 | 0/4 |
| Mean maximal effect 1.6/4 | | | | | |

Drug: Compound of Example 10, Route: i.p.
Dose: 80 mg/kg

| Time | rat 1 | rat 2 | rat 3 | rat 4 | rat 5 |
|---|---|---|---|---|---|
| 0 | + | + | + | + | + |
| 45 | + | — | + | — | — |
| 90 | + | + | + | + | — |
| 110 | + | + | + | + | — |
| 180 | + | + | + | + | + |
| anticataleptic effect | 0/4 | 1/4 | 0/4 | 1/4 | 3/4 |
| Mean maximal effect 1/4 | | | | | |

Summary: The tested compounds of Examples 10, 27 and 36 are all found to be active.

STEREOTYPED BEHAVIOUR IN MICE

Male ICR albino mice weighing 25–30 g were put in cages with a metal grid floor, 4 in each cage. Drugs were injected intraperitoneally and stereotyped behaviour (sniffing, biting, repetitive head movement) was evaluated every 30 min.

Drug Control Symmetrel Route i.p. Dose 50 mg/kg

| Time (min) | Mouse 1 | Mouse 2 | Mouse 3 | Mouse 4 |
|---|---|---|---|---|
| 0 | 0 | 0 | 0 | 0 |
| 30 | 1 | 1 | 1 | 1 |
| 45 | 1 | 1 | 1 | 1 |
| 60 | 2 | 2 | 1 | 1 |
| 90 | 1 | 1 | 2 | 1 |
| 120 | 2 | 2 | 2 | 2 |
| 135 | 2 | 2 | 2 | 2 |
| 150 | 2 | 2 | 2 | 2 |
| 180 | 2 | 2 | 2 | 2 |
| 210 | 2 | 2 | 2 | 1 |
| 240 | 2 | 2 | 2 | 0 |
| Total Score | 17 | 17 | 17 | 13 |
| Mean Score 16 | | | | |

Drug Compound of Example 27 Route i.p. Dose 50 mg/kg

| Time (min) | Mouse 1 | Mouse 2 | Mouse 3 | Mouse 4 |
|---|---|---|---|---|
| 0 | 0 | 0 | 0 | 0 |
| 30 | 0 | 0 | 1 | 0 |
| 45 | 0 | 1 | 1 | 1 |
| 60 | 2 | 2 | 2 | 2 |
| 90 | 2 | 2 | 2 | 2 |
| 120 | 1 | 1 | 0 | 0 |
| 135 | 1 | 1 | 0 | 0 |
| 150 | 1 | 1 | 0 | 0 |
| 180 | 0 | 0 | 0 | 0 |
| 210 | 0 | 1 | 0 | 0 |
| 240 | 0 | 0 | 0 | 0 |
| Total Score | 7 | 9 | 6 | 5 |
| Mean Score 6.5 | | | | |

Drug Compound of Example 10 Route i.p. Dose 50 mg/kg

| Time (min) | Mouse 1 | Mouse 2 | Mouse 3 | Mouse 4 |
|---|---|---|---|---|
| 0 | 0 | 0 | 0 | 0 |
| 30 | 1 | 1 | 1 | 1 |
| 45 | 1 | 2 | 1 | 0 |
| 60 | 1 | 1 | 1 | 1 |
| 90 | 1 | 1 | 1 | 1 |
| 120 | 0 | 0 | 0 | 0 |
| 135 | 0 | 0 | 0 | 0 |
| 150 | 0 | 0 | 0 | 0 |
| 180 | 1 | 1 | 0 | 0 |
| 210 | 1 | 0 | 0 | 0 |
| 240 | 0 | 0 | 0 | 0 |
| Total Score | 6 | 6 | 4 | 3 |
| | | Mean Score 4.75 | | |

Summary: The tested compounds of Examples 10 and 27 were found to be active.

ANTIFUNGAL ACTIVITY IN PLANTS

Figure 1:
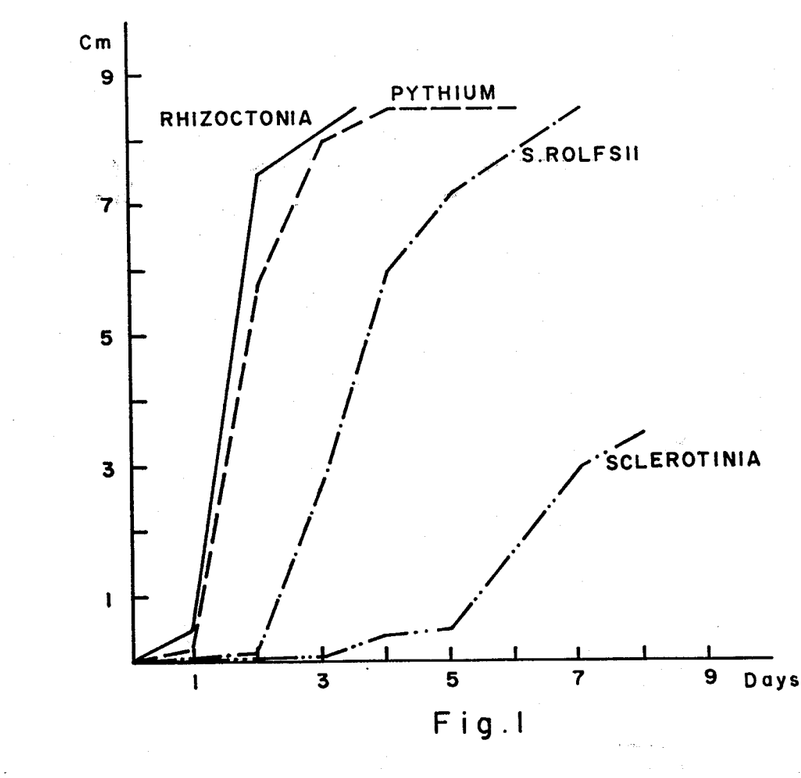
FIG. 1—Anti-fungal activity in plants of the compound of Example 18.
Figure 2:
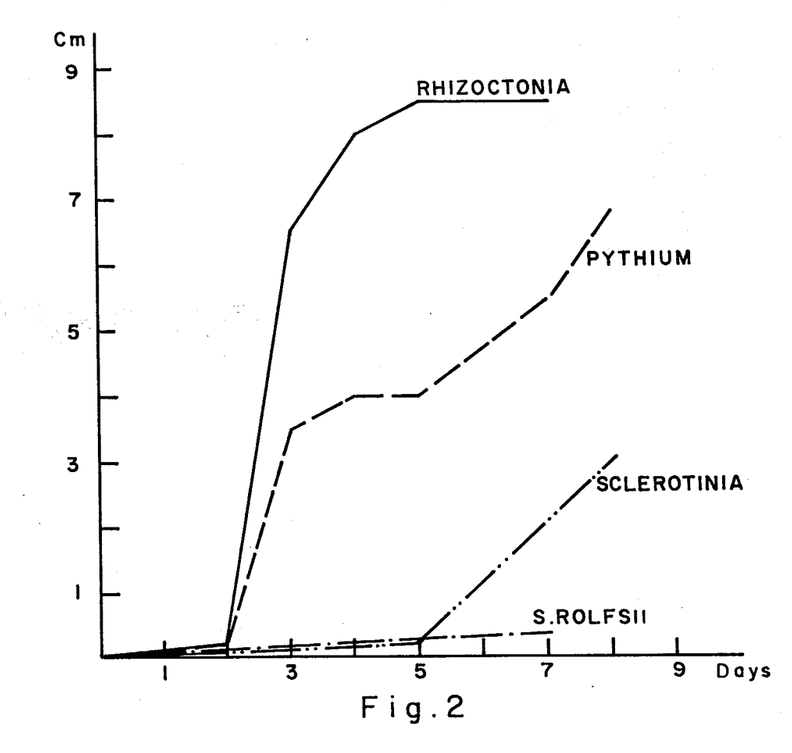
FIG. 2—Anti-fungal activity in plants of the compound of Example 29.

Antiplant fungal activity was tested as follows:
Fungi:
1. Pythium
2. S. rolfsii
3. Rhizoctonia
4. Sclerotinia Evaluation:
Inhibition of growth on solid agar mixed with various concentrations of the tested compounds.
Concentration:
500 μg/ml, 250 μg/ml, 100 μg/ml, 50 μg/ml, 10 μg/ml.
Results:
The compounds of Examples No. 18, 29 were tested and found to inhibit Pythium, Sclerotinia and S. rolfsii in the concentration of 50 μg/ml. The inhibition activities against the above four fungi are plotted in FIG. 1 for the compound of Example 18 and in FIG. 2 for the compound of Example 29. In each case the control growth was 8.5 cm in 3 days.

INHIBITION TEST ON HSV REPLICATION

| Cells | -BSC-1 (Green monkey kidney) |
|---|---|
| Virus | -HSV-1 (Herpes Simplex) |
| Inoculum | -10 PFU/cell |
| Medium | -DMEM + 10% C.S. |

Herpes
J. Levitt & Y. Becker
Virology 31 129-134 (1967)

| Compound of Example No. | Concent. μg/ml | T.L. μg/ml* Toxic Limit | % Inhibition ** |
|---|---|---|---|
| Amant.*** | 50 | 50 | 93 |
| Ex. 27 | 100 | 100 | 99.99 |
| | 50 | | 81 |
| | 25 | | 46 |
| Ex. 36 | 200 | 200 | 98 |
| | 100 | | 0 |
| | 50 | | 0 |
| Ex. 49 | 200 | 100 | 99.9 |
| | 100 | | 92 |
| | 50 | | 60 |
| Ex. 10 | 50 | 50 | 96 |
| | 25 | | 40 |
| | 10 | | 50 |

*T.L. The highest concentration of compound which is completely not toxic.
**% Inhibition of control infected for some time with same virus PFV with no inhibition.
***Amantadine, used as control.

Results

The tested compounds of Examples Nos. 10, 27, 36, 49 were found to inhibit HSV by 96-99% at a concentration of 50-200 μg/ml.

Anti-influenza virus effects (preliminary results)

Method: G. Appleyard and Maber J. of Gen. Virol. 25 351-357 (1974)

The compounds of Examples Nos. 10, 27, 31, 36, 42 were tested and found to be effective against influenza A virus at a concentration of 10-50 μg/ml.

We claim:

1. 2-Adamantyl hydrazine derivative of the formula in which $R_1$ is hydrogen or a lower alkyl group of 1-4 carbon atoms; $R_2$ and $R_3$ together with the nitrogen atom to which they are attached form piperidino, homopiperidino, pyrrolidino or heptamethyleneimine; or a pharmaceutically acceptable acid addition salt thereof.

2. 1-(2'-Adamantylamino)pyrrolidine or a pharmaceutically acceptable acid addition salt thereof, in accordance with claim 1.

3. 1-(2'-Adamantylamino)piperidine or a pharmaceutically acceptable acid addition salt thereof, in accordance with claim 1.

4. 1-(2'-Adamantylamino)homopiperidine or a pharmaceutically acceptable acid addition salt thereof, in accordance with claim 1.

5. 1-(2'Adamantylamino)heptamethyleneimine or a pharmaceutically acceptable acid addition salt thereof, in accordance with claim 1.

6. 1-[(2'-Adamantyl)methylamino]piperidine or a pharmaceutically acceptable acid addition salt thereof, in accordance with claim 1.

7. An antifungal, antiviral, antiprotozoal or antimicrobial composition containing as active ingredient an antifungally, antivirally, antiprotozoally or antimicrobially effective compound according to claim 1 and a pharmaceutical carrier therefor.

* * * * *